(12) United States Patent
Lorimer et al.

(10) Patent No.: US 7,545,148 B2
(45) Date of Patent: Jun. 9, 2009

(54) ELECTROCHEMICAL SENSOR

(75) Inventors: Kevin Lorimer, Abingdon (GB); John Griffiths, Derbyshire (GB); Mark Hyland, Oxford (GB); Herbert Frank Askew, Bicester (GB); John Morton Broughall, Camberley (GB)

(73) Assignee: Oxford Biosensors Limited (GB)

( * ) Notice: Subject to any disclaimer, the term of this patent is extended or adjusted under 35 U.S.C. 154(b) by 239 days.

(21) Appl. No.: 11/660,255

(22) PCT Filed: Aug. 3, 2005

(86) PCT No.: PCT/GB2005/003054

§ 371 (c)(1),
(2), (4) Date: Feb. 15, 2007

(87) PCT Pub. No.: WO2006/030170

PCT Pub. Date: Mar. 23, 2006

(65) Prior Publication Data

US 2007/0285099 A1    Dec. 13, 2007

(30) Foreign Application Priority Data

Aug. 17, 2004 (GB) .................... 0418345.5

(51) Int. Cl.
G01N 27/02 (2006.01)
(52) U.S. Cl. .............. 324/446; 204/400; 205/775
(58) Field of Classification Search ............ 324/446; 204/400; 205/775
See application file for complete search history.

(56) References Cited

U.S. PATENT DOCUMENTS

| | | | |
|---|---|---|---|
| 4,059,406 A | 11/1977 | Fleet | |
| 4,897,162 A | 1/1990 | Lewandowski et al. | |
| 5,980,708 A | 11/1999 | Champagne et al. | |
| 6,558,529 B1 * | 5/2003 | McVey et al. | 205/787 |
| 2003/0201191 A1 | 10/2003 | Kovarsky et al. | |
| 2006/0191788 A1 * | 8/2006 | Wayment et al. | 204/403.01 |

FOREIGN PATENT DOCUMENTS

| | | |
|---|---|---|
| EP | 0 479 033 | 4/1992 |
| GB | 1 448 367 | 9/1976 |
| GB | 2 089 048 | 6/1980 |
| SU | 399775 | 10/1973 |

OTHER PUBLICATIONS

International Search Report corresponding to PCT/GB2005/003054, under date of mailing of Jan. 10, 2006.
Better by Design: The Humanizing Technology Project, Medical Device Technology, Nov. 2003, Oxford Biosensors Ltd., United Kingdom.

* cited by examiner

*Primary Examiner*—Vincent Q Nguyen
(74) *Attorney, Agent, or Firm*—Quarles & Brady LLP; George E. Haas

(57) ABSTRACT

In an electrochemical sensor, the potential difference applied to the electrochemical cell is raised to a measuring value at a rate determined to reduce the transient current. The maximum rate of change of the voltage is set to prevent saturation of an IE converter. The electrochemical cell may contain microelectrodes as working and reference electrodes. The method may be applied to a battery powered, handheld device.

23 Claims, 3 Drawing Sheets

ELECTROCHEMICAL SENSOR

CROSS-REFERENCE TO RELATED APPLICATIONS

Not Applicable

STATEMENT REGARDING FEDERALLY SPONSORED RESEARCH OR DEVELOPMENT

Not Applicable.

BACKGROUND OF THE INVENTION

1. Field of the Invention

The present invention relates to electrochemical sensors and electrochemical sensing methods.

2. Description of the Related Art

In an electrochemical biosensor, a working electrode is used with a counter electrode and a reference electrode, though the latter two may be combined as a pseudo-reference electrode. In the text below the term reference electrode should be construed as indicating pseudo-reference electrodes, unless the context otherwise requires. To make a measurement, a potential difference is applied between the working and reference electrode and the resulting current is measured over a range of voltages. The analyte concentration and analyte species present in a fluid can be derived from current measurements at specific potential differences. Complementary information can be derived from the measured voltammetric peak position (and/or mid point position) and voltammetric peak separation. An electrode that can be used in such biosensors is described in WO 03/056319 (which document is hereby incorporated in its entirety by reference).

It has been discovered that measurements made on such a sensor can suffer from errors, particularly if rapid measurements are to be made on a portable device.

SUMMARY OF THE INVENTION

Accordingly, the present invention provides an electrochemical sensing method comprising:

applying a time-varying potential between working and reference electrodes in electrical contact with a target solution, said time varying potential having a ramp-up period, during which the potential difference increases from substantially zero to a first predetermined potential, and a plateau period during which said potential difference is maintained substantially constant at said first predetermined potential; and sampling the current flowing between said working and reference electrodes during said plateau period.

The present inventors have determined that some errors in measurement derive from applying a step potential to the electrodes. The step rise in potential produces a current spike followed by a decay due in part to the capacitance of the electrodes—the form of the decay is also dependent on the concentration of the target solution and hence cannot be predicted—and the difficulties in sinking a high transient current in a portable device. Thus measurements are taken in a non-steady state and errors result.

Preferably, the rate of potential change in the ramp-up period is less than or equal to about $250 Vs^{-1}$, preferably less than about $150 Vs^{-1}$ and most preferably in the range of from about 5 to $75 Vs^{-1}$. Such a rate reduces the current peak caused by the potential increase so that measurements taken in the plateau period are substantially error-free.

The time-varying potential may further comprise a second ramp-up period during which the potential difference increases from substantially zero to a second predetermined potential, and a second plateau period during which said potential difference is maintained substantially constant at said second predetermined potential; and the method further comprising sampling said current during said second plateau period.

Repeating the ramp-up and measurements provides additional data points to improve averaging. In a particular embodiment the second predetermined potential is of the opposite polarity to the first predetermined potential and has a different magnitude, but in other embodiments the first and second predetermined potentials may have the same polarity.

In a preferred embodiment of the invention, the potential difference in the ramp-up period(s) substantially follows a part of a sinusoidal function, in particular a half of a period. Such a waveform minimises current transients and is also relatively simple to generate in real time.

BRIEF DESCRIPTION OF THE DRAWINGS

The present invention is further described below with reference to an exemplary embodiment and the accompanying drawings, in which.

DETAILED DESCRIPTION OF THE INVENTION

Figure 1:
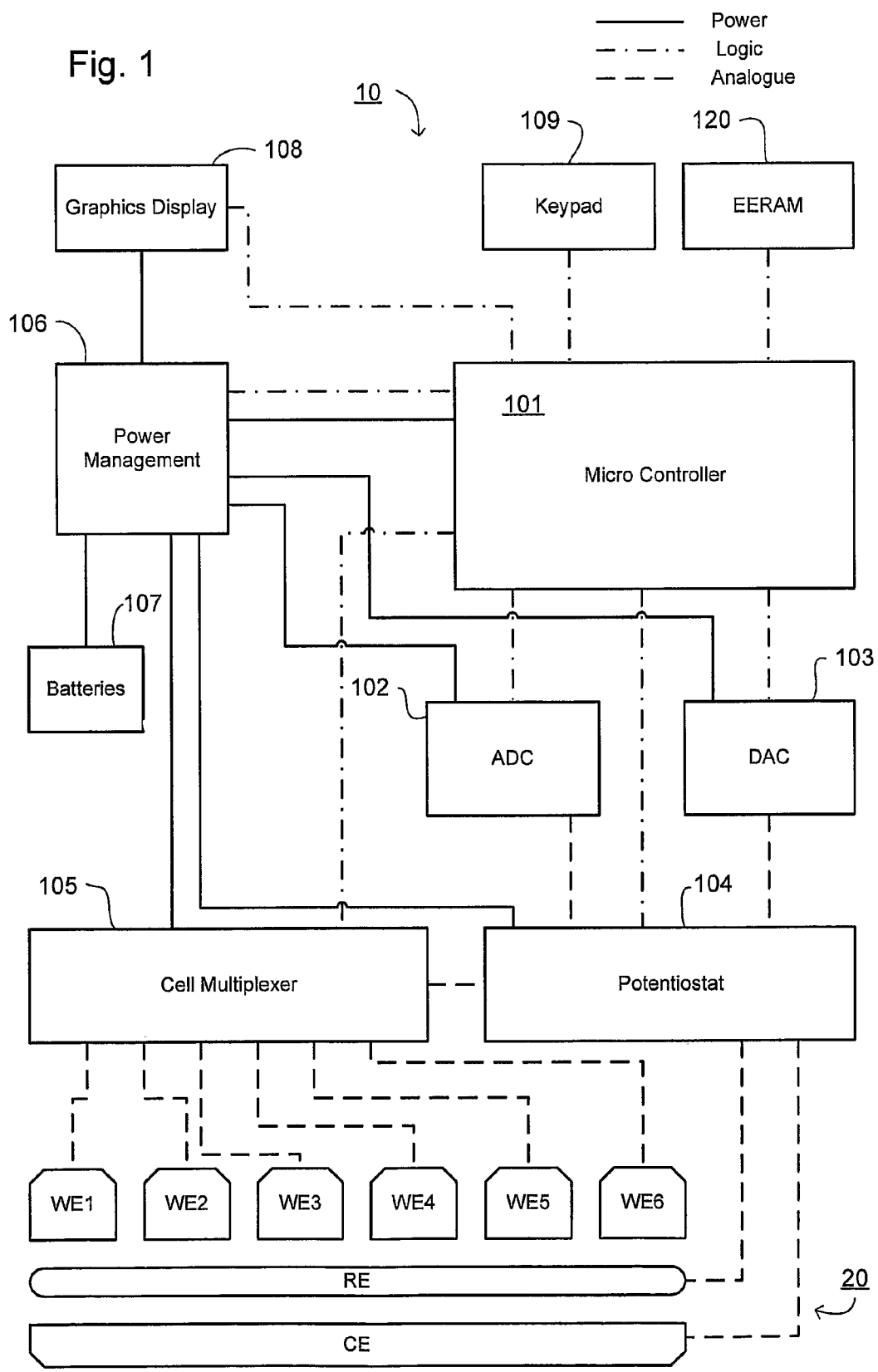
FIG. 1 is a schematic diagram of a portable electrochemical sensor device incorporating the invention.

The sensor device comprises an electronics unit 10 to which is connected an electrode unit 20, which may be disposable. The electrode unit 20 has a plurality of working electrodes WE1-WE6 as well as reference and counter (auxiliary) electrodes RE, CE. More or fewer working electrodes may be used in other embodiments. In some embodiments of the invention, the reference and counter electrodes may be combined as a pseudo-reference electrode. An electrochemical cell is formed between the working and reference electrodes. To make measurements of a target solution that is in electrical connection with the electrodes, various voltages—static and time varying—are applied between ones of the working electrodes and the reference electrodes and the resulting currents detected. For example, ruthenium (Ru) concentration in a sample can be determined by applying a constant voltage and measuring current.

Overall control of the electronics unit 10 of the sensor device is performed by a micro controller 101 which includes an internal memory to store system software. The micro controller may be a dedicated ASIC, an FPGA or a suitably programmed general purpose controller. The micro controller controls a potentiostat 104 via digital to analog converter 103 and receives measurement results from the potentiostat 102 via analog to digital converter 102. The potentiostat 104 applies the desired voltages to the working, reference and counter electrodes WE, RE, CE; a cell multiplexer 105 under the control of microprocessor 101 selects the appropriate one of the working electrodes. The electrodes are preferably micro-electrodes, e.g. having a width of less than about 50 μm, microband electrodes or a micro-electrode array.

A graphics display 108 enables display of operating menus to the user, options being input via keypad 109, and measurement results. An electrically erasable RAM 120 allows for storage of constants and measurement information. A bar code reader may also be provided for input of data, especially of patient information if the sensor is used in a medical or veterinarian application. Interfaces, e.g. conforming RS232, Bluetooth, Ethernet, USB, or WiFi (IEEE 802.11a, b, g, etc.) standards, may be provided for connection to printers, networks and other devices, e.g. patients records systems. The separately illustrated circuits may be combined onto one or more ASICs or FPGAs.

Power is supplied from batteries 107 under the control of a power management unit 106 that optimises battery life and controls recharging of the batteries.

When a desired potential difference is to be applied to the electrochemical cell, if the output of the potentiostat is simply raised in a step function to that potential, a transient current will occur. The size of the initial current peak and the rate of decay will depend on factors such as the applied potential, as well as the capacitance, inductance and resistance of the electrochemical cell and the conductors leading to it. The capacitance and resistance of the electrochemical cell will be determined in part by the concentration of ions in the sample to be measured and hence the shape of the transient current cannot be predicted with sufficient accuracy. Current saturation in the amplifier of the potentiostat adds further complication. If current measurements are taken before the transient current has fully decayed, errors will result. In a portable device it is difficult to provide a large current sink to absorb the transient current rapidly so that a significant delay must be observed before measurements are taken. This increases measurement times which is particularly undesirable if multiple measurements are to be taken of a given sample.

Figure 2:
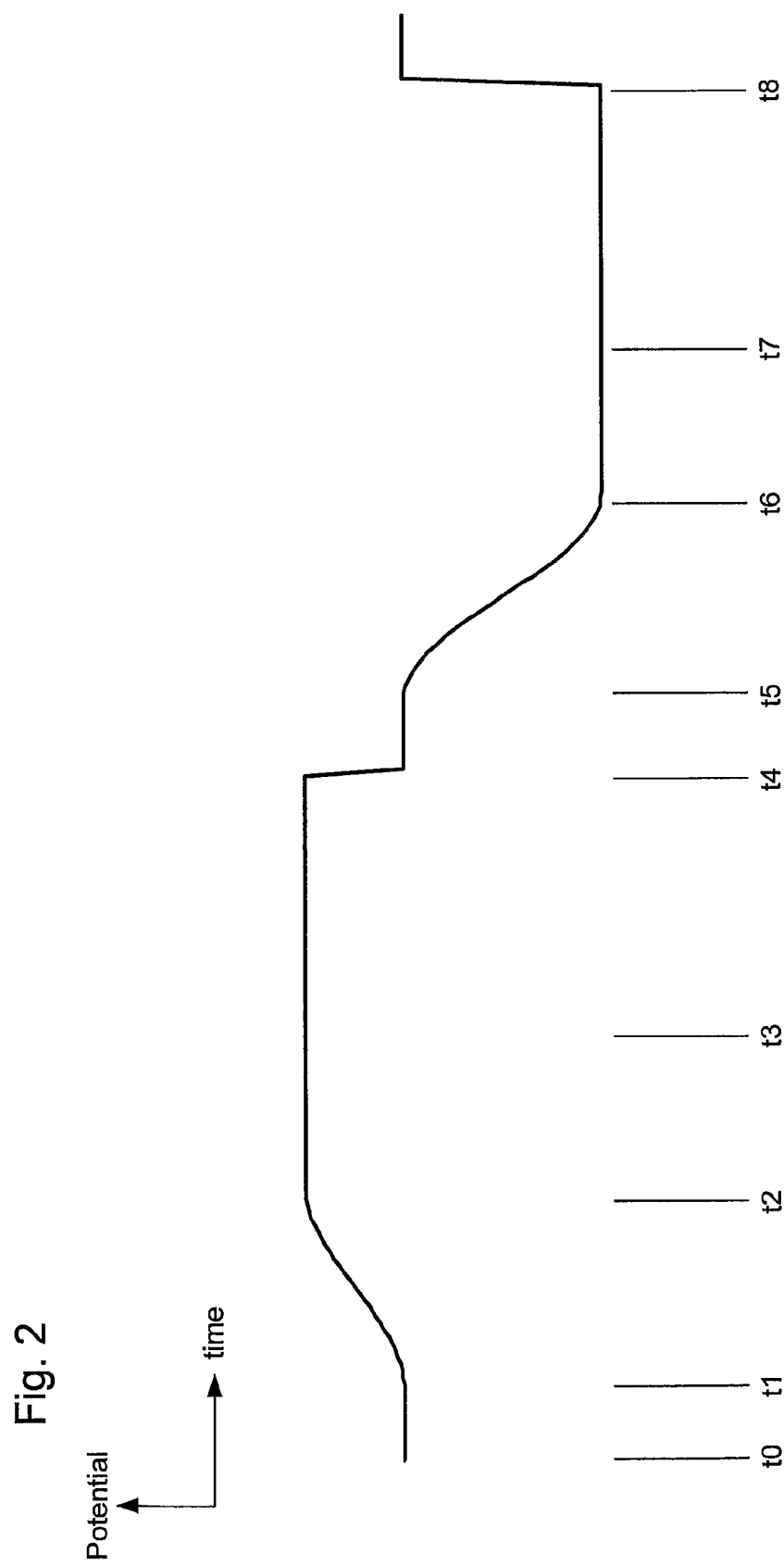
FIG. 2 is a graph of potential vs. time of a waveform applied to electrodes in an embodiment of the invention.

To avoid the generation of substantial transient currents, the present embodiment applies a potential waveform as shown in FIG. 2 to the electrochemical cell. The waveform may be generated by providing a series of digital values as inputs to the digital to analog converter 103 which then drives the potentiostat 104. Suitable digital values can be calculated by a simple algorithm executed by the microcontroller 101 or calculated in advance and stored in memory.

The waveform applied to the electrochemical cell has two parts, in the first (t0 to t4) a positive potential is applied to the cell and in the second (t4 to t8) a negative potential is applied. In this example the second part has a similar structure to the first part but opposite polarity and a different magnitude. However, the second part may instead have the same polarity and magnitude and may also be omitted if not required—e.g. to provide additional measurements.

In both parts of the waveform, after an initial delay, t0 to t1, at which the voltage is held at substantially 0 the waveform ramps up to a desired voltage $+V_1$ in the period t1 to t2. The voltage in this period conforms to a part of a sinusoidal curve—approximately half a cycle—to minimise the transient current, however other waveforms may be applied. After the ramp-up portion there is a plateau, t2 to t4, during which the potential applied to the cell is held substantially constant. The current through the cell is sampled during the latter part of the plateau, between times t3 and t4. The number of samples and the data rate may be chosen to suit the specific electrochemical measurement being made but for example 20 samples may be taken at a rate of about 300 Hz. The potential difference applied to the electrochemical cell during measurements, i.e. the plateau potential, will depend on the species to be detected an/or measured. Potentials in the range of ±2V (measured against an Ag/AgCl electrode) are suitable.

As mentioned above, the negative-going part of the example waveform has ramp-up and plateau portions t5 to t6 and t6 to t8 that are inversions of the corresponding portions of the positive-going part of the example waveform. Of course in other embodiments, the second part of the waveform may have the same polarity as the first part and/or a different magnitude.

During the ramp-up portion, the maximum slope is determined to keep the transient current below levels that can be sunk in the amplifier of the potentiostat. For example, a rate of about $50 Vs^{-1}$ is suitable. This would provide a rise from 0 to ±0.5V in about 100 ms. A step potential, in which the potential is raised in less than 1 ms could result in a rate of $600 Vs^{-1}$.

At the end of the plateau, the voltage can be returned to zero as rapidly as desired if transients will not affect any further measurements but a soft ramp down may also be used, especially if other measurements are to be performed soon after.

Figure 3:
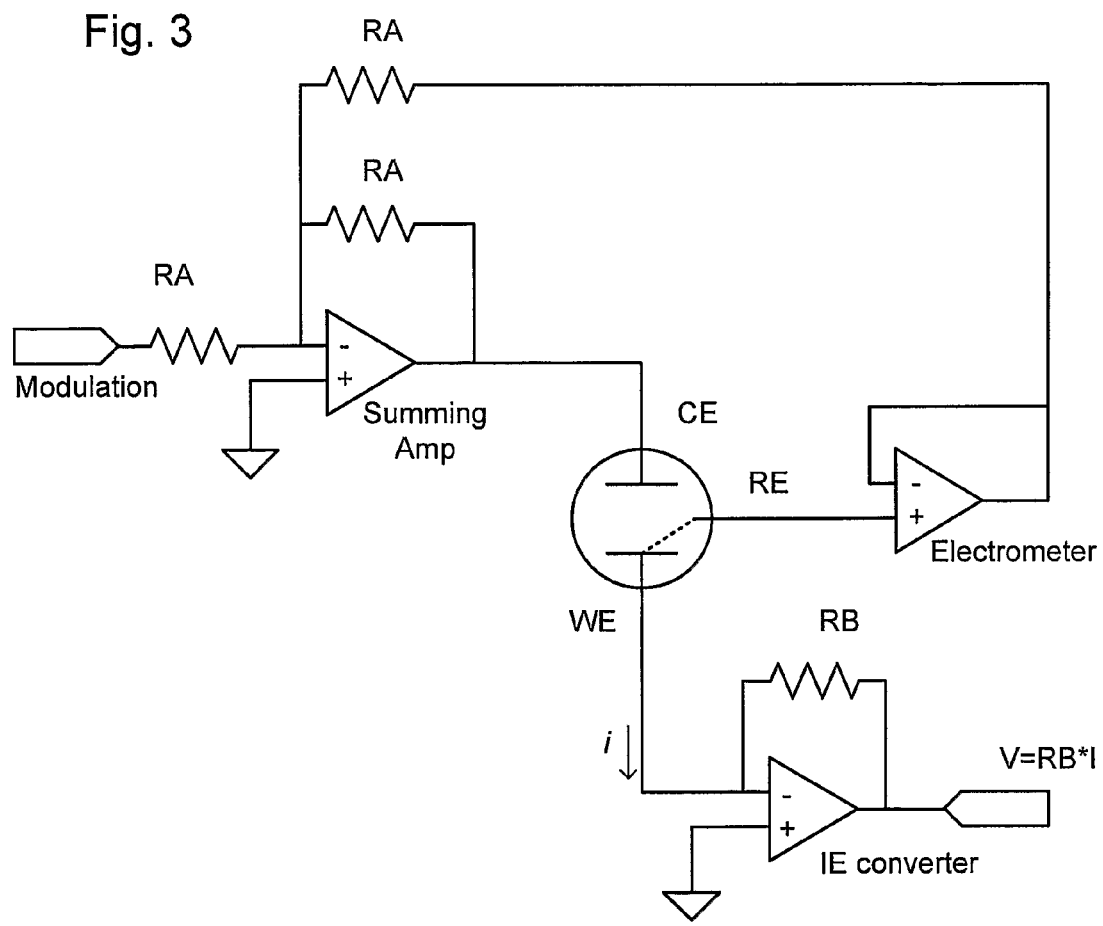
FIG. 3 is schematic of a basic potentiostat.

As the aim of the ramp-up portion is to prevent overload of the IE converter that forms part of the potentiostat, the required rate of potential change can be determined from consideration of a basic potentiostat circuit, such as that shown in FIG. 3. The modulation input to the potentiostat is shown at the right hand side of the figure and is amplified and applied to the common electrode CE of the electrochemical cell. The electrometer buffers the electrochemical potential of the reference electrode RE and feeds this potential back into a summing amplifier such that the potential of the counter electrode is maintained relative to the reference electrode. The IE converter converts the current i flowing out of the working electrode to a voltage output $V=RB*i$, where RB is the value of the feedback resister of the IE converter, which is essentially an operational amplifier current follower circuit.

In a practical circuit the maximum voltage output of the operational amplifier is limited by the power supply voltage and the characteristics of the operational amplifier selected. It is implicit that the voltage output of an operational amplifier cannot exceed its power supply voltage.

Given that the voltage output of the IE converter is given by $V=RB*i$. There will be a maximum value of i, which can be input to the circuit, which is defined by the power supply voltage. In the situation where i exceeds this value the voltage output of the operational amplifier is limited by the power supply voltage. This output is no longer representative of the current i. The effect on the negative input should also be considered. In normal operation the potential at the negative input is zero, being the sum of i and the current through RB. In the overload condition the current though RB is no longer sufficient to match i, the result of this is that the potential at the negative input is no longer held at zero, but rises towards the potential at CE in three electrode systems, or shifts with the pseudo-reference electrode in two electrode systems. This causes the potentiostat to lose potential control and thus the electrochemical cell is no longer held at the desired potential. It follows that the current though the electrochemical cell is then limited by the saturation of the IE converter. Thus, the maximum ramp-up rate should be set to prevent saturation of the IE converter, which effectively means that the transient current should not be greater than the maximum current to be measured.

This condition is particularly true in battery powered instruments where the power supply voltages are required to be a minimum to conserve power and reduce the circuitry.

Whilst the invention has been described above in relation to a specific embodiment, the present invention may be embodied in other forms. For example, other functions may be used to define the ramp-up, including a linear sweep, logarithmic functions, sigmoidal functions, hyperbolas, logistic functions, Weibull functions, Gompertz growth model, Hill function, Chapman model. Polarities in this document are defined using IUPAC conventions but the results can readily be converted to other conventions. The scope of the invention is therefore determined by the appended claims rather than the foregoing description.

The invention claimed is:

1. An electrochemical sensor device comprising:
   a potentiostat for applying a potential between working and counter electrodes in electrical contact with a target solution and sampling the current flowing between the electrodes;
   a controller for controlling the potentiostat so that it applies a time varying potential having a ramp-up period, during which the potential difference increases from a first predetermined potential to a second predetermined potential, followed by a plateau period during which said potential difference is maintained substantially constant at said second predetermined potential and samples the current flowing between said working and counter electrodes for measurement purposes, only during said plateau period.

2. A device according to claim 1 wherein the controller is adapted to control the potentiostat so that the rate of potential change in the ramp-up period is less than or equal to about $250Vs^{-1}$, preferably less than about $150Vs^{-1}$ and most preferably in the range of from about 5 to $75Vs^{-1}$.

3. A device according to claim 1 wherein the controller is further adapted to control the potentiostat so that the time-varying potential further comprises a second ramp-up period during which the potential difference increases from a third predetermined potential to a fourth predetermined potential, and a second plateau period during which said potential difference is maintained substantially constant at said fourth predetermined potential; and to sample said current during said second plateau period.

4. A device according to claim 3 wherein the fourth predetermined potential is of the opposite polarity to the second predetermined potential.

5. A device according to claim 1 wherein the potential difference in the ramp-up period(s) substantially follows a part of a sinusoidal function, in particular half a period.

6. A device according to claim 1 wherein the potential difference in the ramp-up period(s) substantially follows a part of a function selected from the group comprising a linear sweep, logarithmic functions, sigmoidal functions, hyperbolas, logistic functions, Weibull functions, a Gompertz growth model, a Hill function, and a Chapman model.

7. A device according to claim 1 wherein said first potential is an open circuit potential.

8. A device according to claim 1 wherein said third potential is an open circuit potential.

9. A device according to claim 1 wherein said electrodes are micro-electrodes, microband electrodes or a micro-electrode array.

10. A device according to claim 1 further comprising a waveform generator arranged to generate the waveform of the potential difference in the ramp-up period(s) in real time.

11. A device according to claim 1 further comprising a memory for storing a plurality of values representing the waveform to be applied to said electrodes and wherein said controller is adapted to read said values in sequence from said memory.

12. A device according to claim 1 wherein said device is battery powered and hand held.

13. An electrochemical sensing method comprising:
    applying a time-varying potential between working and reference electrodes in electrical contact with a target solution, using a potentiostat containing an IE converter said time varying potential having a ramp-up period, during which the potential difference increases from a first predetermined potential to a second predetermined potential, followed by a plateau period during which said potential difference is maintained substantially constant at said second predetermined potential; and
    sampling the current flowing between said working and counter electrodes for measurement purposes, only during said plateau period,
    wherein the inncrease of the potential difference in the ramp-up period has a maximum rate that is set to prevent saturation of the IE converter.

14. A method according to claim 13 wherein the rate of potential change in the ramp-up period is less than or equal to about $250Vs^{-1}$, preferably less than about $150Vs^{-1}$ and most preferably in the range of from about 5 to $75Vs^{-1}$.

15. A method according to claim 13 wherein the time-varying potential further comprises a second ramp-up period during which the potential difference increases from a third predetermined potential to a fourth predetermined potential, and a second plateau period during which said potential difference is maintained substantially constant at said fourth predetermined potential; and the method further comprising sampling said current during said second plateau period.

16. A method according to claim 15 wherein the fourth predetermined potential is of the opposite polarity to the second predetermined potential.

17. A method according to claim 15 wherein the fourth predetermined potential is of a different magnitude than the second predetermined potential.

18. A method according to claim 13 wherein the potential difference in the ramp-up period(s) substantially follows a part of a sinusoidal function, in particular half a period.

19. A method according to claim 13 wherein the potential difference in the ramp-up period(s) substantially follows a part of a function selected from the group comprising a linear sweep, logarithmic functions, sigmoidal functions, hyperbolas, logistic functions, Weibull functions, a Gompertz growth model, a Hill function, and a Chapman model.

20. A method according to claim 13 wherein the waveform of the potential difference in the ramp-up period(s) is calculated in real time.

21. A method according to claim 13 wherein said first potential is an open circuit potential.

22. A method according to claim 13 wherein said third potential is an open circuit potential.

23. A method according to claim 13 wherein said electrodes are micro-electrodes, microband electrodes or a micro-electrode array.

* * * * *